US 6,984,375 B2

(12) United States Patent
Holland et al.

(10) Patent No.: US 6,984,375 B2
(45) Date of Patent: Jan. 10, 2006

(54) NUCLEI DENSITY AND NUCLEI AREA METHODS FOR DETERMINING EFFECTS OF A BOTULINUM TOXIN ON MUSCLES

(75) Inventors: James M. Holland, Dana Point, CA (US); Edward Chow, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 55 days.

(21) Appl. No.: 10/208,165

(22) Filed: Jul. 29, 2002

(65) Prior Publication Data

US 2003/0026760 A1 Feb. 6, 2003

Related U.S. Application Data

(60) Provisional application No. 60/309,988, filed on Aug. 3, 2001.

(51) Int. Cl.
*A61K 49/00* (2006.01)

(52) U.S. Cl. .......................... 424/9.2; 424/239.1; 435/6; 536/23.1; 800/8

(58) Field of Classification Search ................. 424/9.2, 424/239.1, 93.6, 93.2, 184.1, 810, 443, 430.1, 424/282.1, 236.1, 247.1, 434, 45, 78.02; 435/6, 320.1, 69.4, 287.2, 440, 7.2, 7.21, 435/29, 40.5, 40.51, 288.3, 288.4, 7.1, 7.22, 435/7.23, 7.24, 7.9, 7.92, 7.93, 7.94, 7.95, 435/842; 536/24.3, 23.1; 514/44, 2, 14, 825, 514/885, 866, 826, 937, 944; 530/350, 387.1, 530/389.1; 800/8; 436/546, 172, 800; 604/51, 604/501; 128/898; 250/205; 382/133; 356/300, 356/326

See application file for complete search history.

(56) References Cited

U.S. PATENT DOCUMENTS 5,158,976 A * 10/1992 Rosenberg .................. 514/561
5,183,462 A * 2/1993 Borodic ...................... 604/506
5,298,019 A * 3/1994 Borodic ...................... 604/511
5,314,805 A * 5/1994 Haugland et al. ............. 435/29
5,401,243 A * 3/1995 Borodic ...................... 604/511
5,548,661 A * 8/1996 Price et al. ................. 382/133

(Continued)

FOREIGN PATENT DOCUMENTS

WO 99/03483 * 1/1999

OTHER PUBLICATIONS

Limousin, Patricia et al, Treatment of dystonia occurring in Parkinsonian syndromes by *botulinum* toxin, Eur. Neurol. 1997, vol. 37, pp. 66–67.*

Duchen, LW, Journal of the neurological sciences, Sep. 1971, vol. 14(1), p 47–74, electron microscopic structure of slow and fast skeletal muscle fibres after the local injection of *botulinum* toxin (cell nucleus descriptor) (abstracts only).*

Sesardic, D et al, Pharmacology and Toxicology, 1996, vol. 78, pp. 283–288.*

Voytik, SL et al, Development Dynamics, vol. 198, pp. 214–224, 1993.*

Ellies, M et al, J Oral Maxillofac. Surg. vol. 58, pp. 1251–1256, 2000.*

Borodic et al, 1992, *Botulinum* and Tetanus Neurotoxins (ed BR DasGupta, Plenum Press, New Y rk)pp623–645.*

(Continued)

*Primary Examiner*—Lynette R. F. Smith
*Assistant Examiner*—Ginny Allen Portner
(74) *Attorney, Agent, or Firm*—Stephen Donovan

(57) ABSTRACT

Methods for determining the effect of a *Clostridal* toxin on muscle are disclosed. In particular, methods for determining a potency and/or diffusion of a toxin based on a nuclear index and/or the extent of muscle atrophy are disclosed.

11 Claims, 15 Drawing Sheets

U.S. PATENT DOCUMENTS

| | | | | | |
|---|---|---|---|---|---|
| 5,696,077 | A | * | 12/1997 | Johnson et al. | |
| 5,766,605 | A | * | 6/1998 | Sanders et al. | 424/239.1 |
| 5,856,665 | A | * | 1/1999 | Price et al. | 250/205 |
| 6,143,306 | A | * | 11/2000 | Donovan | 424/236.1 |
| 6,235,289 | B1 | * | 5/2001 | Aoki et al. | 424/236.1 |
| 6,306,403 | B1 | * | 10/2001 | Donovan | 424/239.1 |
| 6,309,883 | B1 | * | 10/2001 | Minshull et al. | 435/440 |
| 6,358,926 | B2 | * | 3/2002 | Donovan | 514/14 |
| 6,416,765 | B1 | * | 7/2002 | Donovan | 424/236.1 |
| 6,416,959 | B1 | * | 7/2002 | Giuliano et al. | 435/7.2 |
| 6,429,189 | B1 | * | 8/2002 | Borodic | 514/2 |
| 6,485,413 | B1 | * | 11/2002 | Boppart et al. | 600/160 |
| 6,620,415 | B2 | * | 9/2003 | Donovan | 424/239.1 |
| 6,673,024 | B2 | * | 1/2004 | Soito et al. | 600/573 |
| 2002/0137886 | A1 | * | 9/2002 | Lin et al. | 530/350 |
| 2002/0197278 | A1 | * | 12/2002 | Allison | 424/239.1 |
| 2003/0026760 | A1 | * | 2/2003 | Holland et al. | 424/9.2 |
| 2003/0032069 | A1 | * | 2/2003 | Muraca | 435/7.21 |
| 2004/0228881 | A1 | * | 11/2004 | Oliver et al. | 424/239.1 |

OTHER PUBLICATIONS

Ohishi, I et al, Histopathological effect of botulinum C2 toxin on mouse intestines. Infection Immunity, vol. 43(1), pates 54–58, 1984.*

Trachtenberg, J.T. Developemental Biology, vol. 196, pp. 193–203, 1998, Fiber Apoptosis in Developing Rat Muscles is regulated by activity, neurogulin.*

Van den Bergh, P et al, Brain Research, vol. 707, pp. 206–212, 1996, Effect of muscle denervation on the expression of substance P in the ventral raphe–spinal pathway of the rat.*

Borodic, Gary E et al (reference of record).*

Chen et al (2002, Figure 7, p. 1442, and abstract; reference of record).*

Coffield, J.A. et al, The Journal of Pharmacology and Experimental Therapeutics, vol. 289, No. 3, pp. 1509–1516, 1999.*

Doggweiler, R et al, The Postate, vol. 37, pp. 44–50, 1998.*

Borodic, Gary E et al, *Botulinum* and Tetanu Neurotoxins, Edited by B.R. DesGupta, Plenum Press, New York 1992, pp. 623–645.*

Chen, Chen–Ming et al, J. Appl. Physiol., vol. 93, p. 1437–1447, Jun. 30, 2002.*

Spencer, RF et al, Arch. Ophthalmol, vol. 105, Dec. 1987, pp. 1703–1711.*

Paisson, EM et al, The Journal of Biological Chemistry, vol. 275(11), Mar. 17, pp. 7818–7825, 2000.*

Parratte, B etal, Surgical and radiological anatomy, (Germany), May 2002, vol. 24(2), pp. 91–96.*

Rokx, JT et al, Acta anatomica (Switzerland), 1987, vol. 129(4), pp. 333–336.*

Ellies, Met al, European Federation of Oto–Rhino–Laryngological Societies, 1999, vol. 256(3), pp. 148–152.*

Giovanoli, Pe tal, Plastic and reconstructive surgery, Aug. 200, vol. 106(2), pp. 383–392.*

Hill, RR et al, Journal of neurocytology, Mar. 1991, vol. 20(3), pp. 165–182.*

Hott, JS et al, Neurology, Feb. 1998, vol. 50(2), pp. 485–491.*

Kranjc, BS et al, Investigative ophthalmology & visual science, Dec. 2001, vol. 42(13), pp. 3158–3164.*

Lu, L et al, Plastic and reconstructive surgery, Jun. 1998, vol. 101(7), pp. 1875–1880.*

Mendler, L et al, Neromuscular disorders, Dec. 1998, vol. 8(8),pp. 533–541.*

Mohan, M et al, Br. J. Ophthalmol, 1999, Voo. 83, p. 1306+.*

Schwab, ME et al (1976) Brain Research, Mar. 26, vol. 105(2), pp. 213–227.*

Bhatia, KP et al, J. Neurol. Neurosurg. Psychiatry, 1999, vol. 67, pp. 90–93.*

Witzemann, V et al, FEBS Letters, (Netherlands) May 6, 1991, vol. 282(2), pp. 259–264, Differential regulation of MyoD and myogenin mRNA levles by nerve induced muscle activity.*

Ansved, T, Neurology, (United States) May 1997, vol. 48(5), pp. 1440–1442, Muscle fiber atropy in leg muscles after *botulinum* toxin type A treatment of cervical dystonia.*

Aoki, K.R., *Preclinical update on Botox® (botulinum toxin type A)—purified neurotoxin complex relative to other botulinum neurotoxin preparations,* European Journal of Neurology 1999, 6 (suppl 4):S3–S10.

Barry, B.W., *Novel mechanisms and devices to enable successful transdermal drug delivery,* European Journal of Pharmaceutical Sciences, 14 (2001) 101–114.

Bigalke, H., et al., *Botulinum A neurotoxin inhibits non–cholinergic synaptic transmission in mouse spinal court neurons in culture,* Brain Res. 1985;360:318–24.

Bigalke, H., et la., *Tetanus toxin and botulinum A toxin inhibit release and uptake of carious transmitters, as studied with particulate preparations from rat brain and spinal cord,* Naunyn Schmiedebergs Arch Pharmacol, 1981: 316–244–51.

Boyd, R.S., et al., *The insulin secreting•–cell line, HIT–15 contains SNAP–25 which is a target for botulinum neurotoxin–A,* Movement Disorders, vol. 10, No. 3, 1995, pp. 376.

Garcia, A., et al., *Cosmetic denervation of the muscles of facial expression with botulinum toxin,* Dermatol Surg 1996, 22: pp 39–43.

Gonnelle–Gispert, C., et al., *SNAP–25a and –25b isoforms are both expressed in insulin–secreting cells and can function in insulin secretion,* Biochem. J. (1999) 339, 159–165.

Habermann, E., et al., *Tetanus toxin and botulinum A and C neurotoxins inhibit noradrenaline release from cultured mouse brain,* J. of Neurochemistry, 51, 522–527 (1988).

Habermann, E., *Inhibition byb tetanus and botulinum A toxin of the release of [$^3H$]noradrenaline and [$^3H$]GABA from rat brain homogenate,* Experientia Mar. 15, 1988:44(3):224–6.

Jankovic, J., et al., *Therapy with Botulinum Toxin,* Marcel Dekker, Inc., 1994, p. 5.

Li, F., et al., *Formation of binucleated cardiac myocytes in rat heart II. Cytoskeletal organization,* J. Mol Cell Cardiolo 29, 1553–1565 (1997).

Lim, D.A., et al., *Interaction between astrocytes and adult subventricular zone precursors stimulates neurogenesis,* Proc. Natl. Acad. Sci. USA, vol. 96, pp 7526–7531, Jun. 1999, Neurobiology.

Luna, L.E., *Manual of histologic staining methods of the armed forces institute of pathology,* $3^{rd}$ ed., 1968, Chapter 6, McGraw–Hill, pp. 72–99.

Manual of Histologic and Special Staining Technics, McGraw–Hill Book Co., The Blakiston Division, $2^{nd}$ Ed., (1960) Chp. 6, *Stains for Connective Tissue,* pp. 55–95.

Marchese–Ragona, R., et al., *Management of Parotid Sialocele with Botulinum Toxin,* The Laryngoscope, Aug. 1999, 109, pp. 1344–1346.

Marjama–Lyons, et al., *Tremor–predominant Parkinson's disease*, Drugs and Aging Apr. 2000; 16(4): 273–278.

Naumann, M., et al., *Botulinum toxin type A in the treatment of focal, axillary and palmar hyperhidrosis and other hyperhidrotic conditions*, European Journal of Neurology, 1999 6 (suppl 4): S111–S115.

Pearce, L.B., et al., *Pharmacologic characterization of botulinum toxin for basic science and medicine*, Toxicon, 1997 vol. 35, No. 9, pp. 1373–1412.

Pearce, L.B., et al., *Measurement of botulinum toxin activity: evaluation of the lethality assay*, Toxicology and Applied Pharmacology 128, 60–77, (1994).

Sesardic, D., et al., *Refinement and validation of an alternative bioassay for potency testing of therapeutic botulinum type A toxin*, Pharmacol Toxicol 1996; 78(5): 283–8.

Sanchez–Prieto, J., et al., *Botulinum toxin A blocks glutamate exocytosis from guinea–pig cerebral cortical synaptosomes*, Eur J. Biochem Jun. 1987; 165(3):675–681.

Schantz, E., et al., *Standardized assay for Clostridium botulinum toxins*, J. Assoc of Anal Chem. 1978; 61(1) pp 96–9.

Schantz, E., et al., *Properties and use of botulinum toxin and other microbial neurotoxins in medicine*, Microbiological Reviews, Mar. 1992 p. 80–99, vol. 56, No. 1.

Singh, B.R., *Critical aspects of bacterial protein toxins*, Natural Toxins II, 1996 Plenum Press, NY, Chp. 4, pp. 63–84.

Voytik, S.L., et al., *Differential expression of muscle regulatory factor genes in normal and denervated adult rat hind limb muscles*, Developmental Dynamics (1993) 198:214–224.

Adler, M., et al., *Persistence of botulinum neurotoxin A demonstrated by sequential administration of serotypes A and E in rat EDL muscle*, Toxicon 39 (2001) 233–243.

Hámijian, J.A., et al., Abstract: *Serial neurophysiological studies of intramuscular botulinum–A toxin in humans*, Database Medline PubMed ID: 7969239, Dec. 1994 (1994012).

Hogwei, D., et al., *Morphologic changes in extraocular muscles after injection botulinum A toxin*, Clin Ophthal Res. Apr. 2000, vol. 18, No. 2, pp. 140–142.

Pinter, M.J., *Axotomy–like changes in cat motoneuron electrical properties elicited by botulinum toxin depend on the complete elimination of neuromusclar transmission*, Journal of Neuroscience, Mar. 1991, 11(3): pp. 657–666.

Samuel, D.P., *Hemihypertrophy and poorly differentiated embryonal rhabdomyosarcoma of the pelvis*, Medical and Pediatric Oncology 32: 38–43 (1999).

Braun, Thomas, et al., Differential expression of myogenic determination genes in muscle cells: possible autoactivation by the Myf gene products, *EMBO Journal*, vol. 8, #12 pp. 3617–3625, 1989.

Chomczynski, P., et al., Single–step method of RNA isolation by acid guanidinium thiocyanate–phenol–chloroform extraction, *Analytical Biochemistry*, 162, 156–159 (1987).

David, R.L., et al., Expression of a single transfected cDNA converts fibroblasts to myoblasts, *Cell*, vol. 51, 987–1000, Dec. 24, 1987.

Koppe, R.I., et al., cDNA clone and expression analysis of rodent fast and slow skeletal muscle troponin I mRNAs*, *The Journal of Biological Chemistry*, vol. 264, No. 24, Aug. 25, 1989 pp. 14327–14333.

Lehrach, H., et al., RNA molecular weight determinations by gel electrophoresis under denaturing conditions, a critical reexamination, *Biochemistry*, vol. 16, No. 21, 1977, pp. 4743–4751.

Wright, W.E., et al., Myogenin, a factor regulating myogenesis, has a domain homologous to MyoD, *Cell*, Vo. 56, Feb. 24, 1989, pp. 607–617.

* cited by examiner

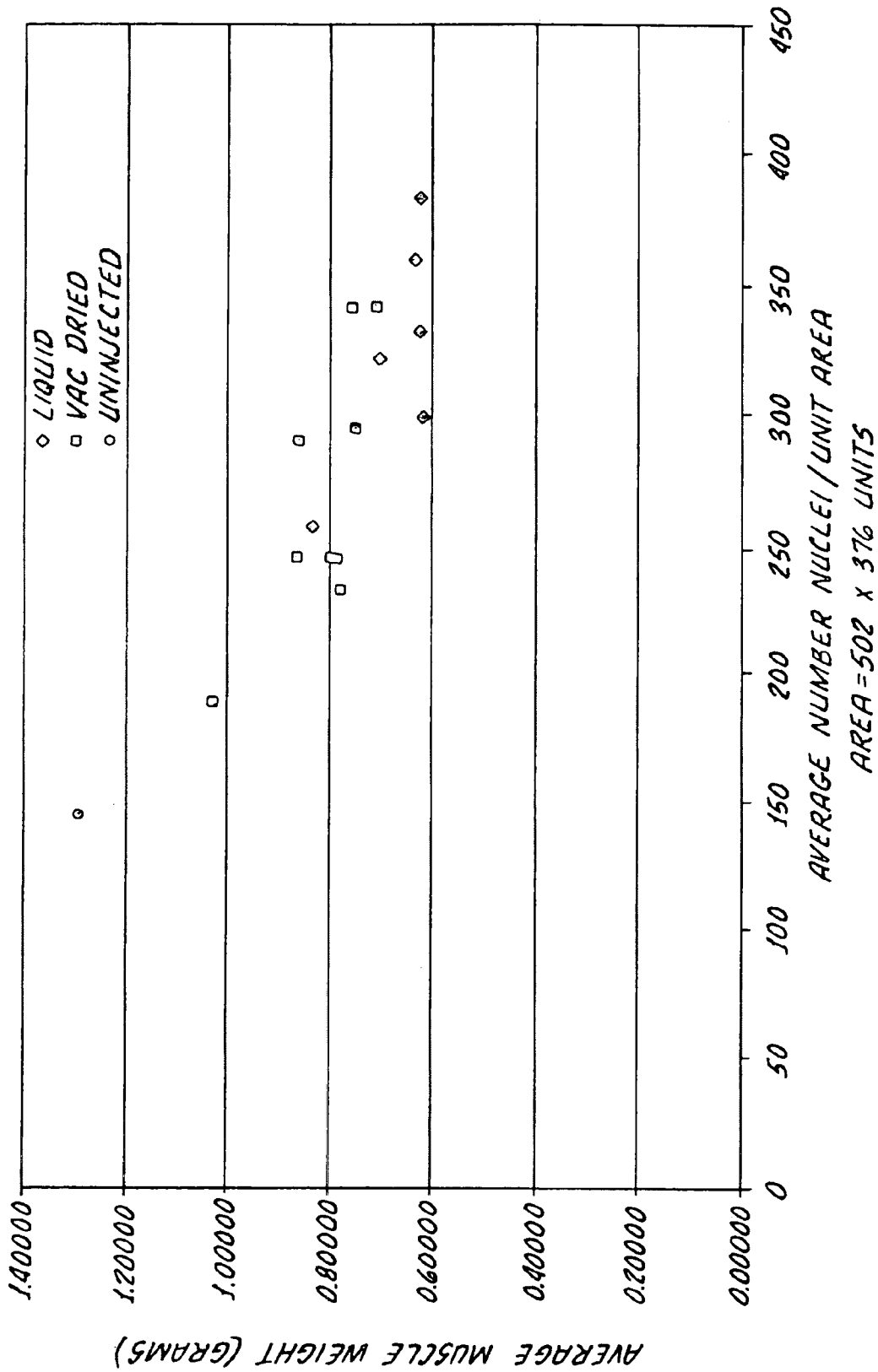

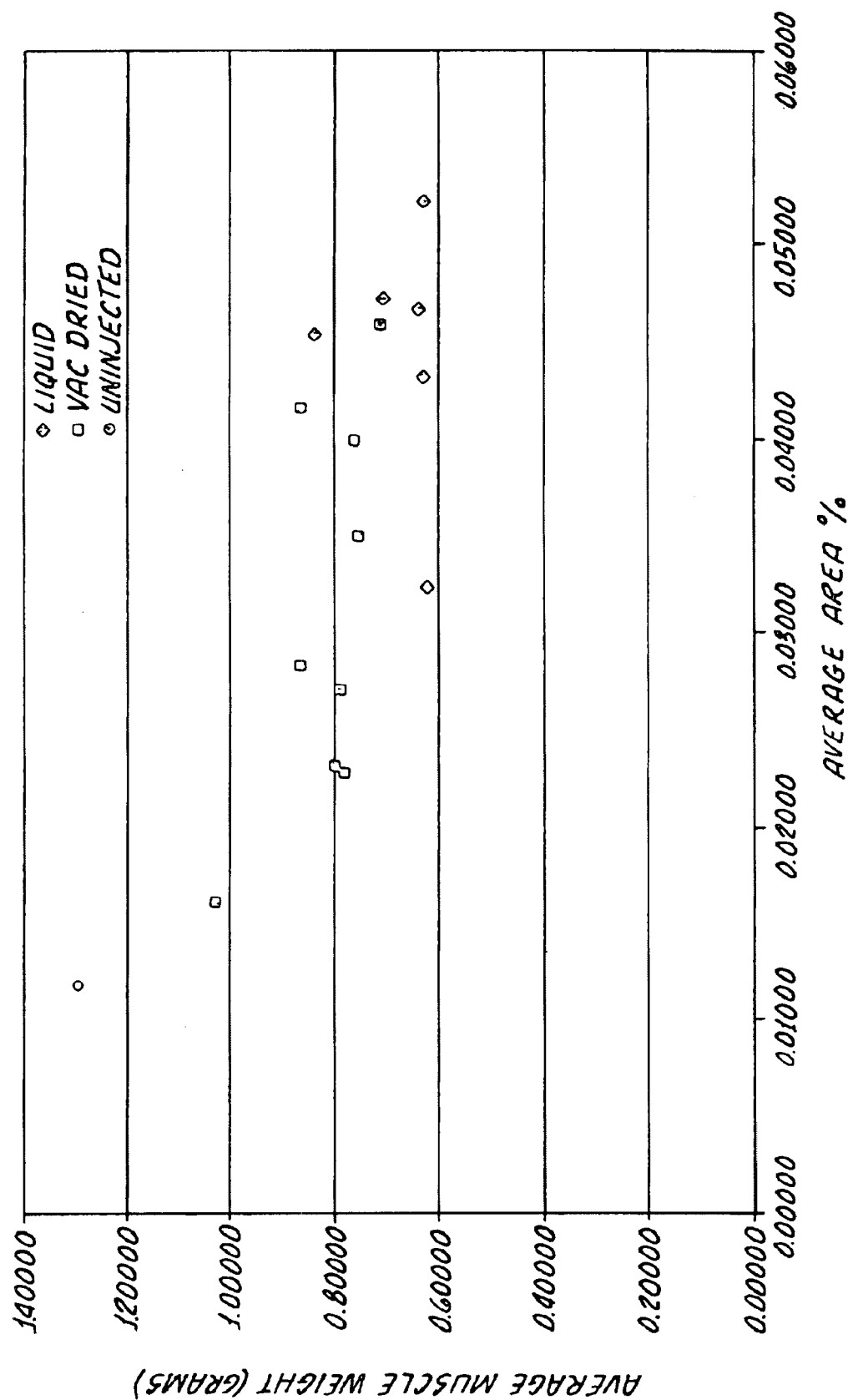

FIG. 5A.   2101L OUTER
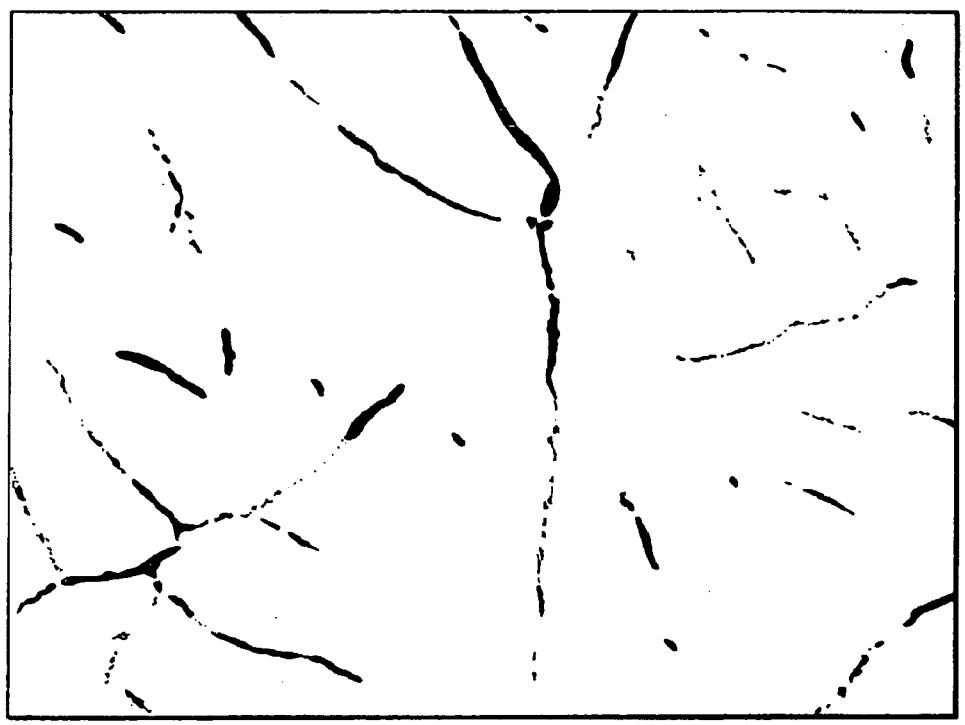
FIG. 5B.   2101L OUTER
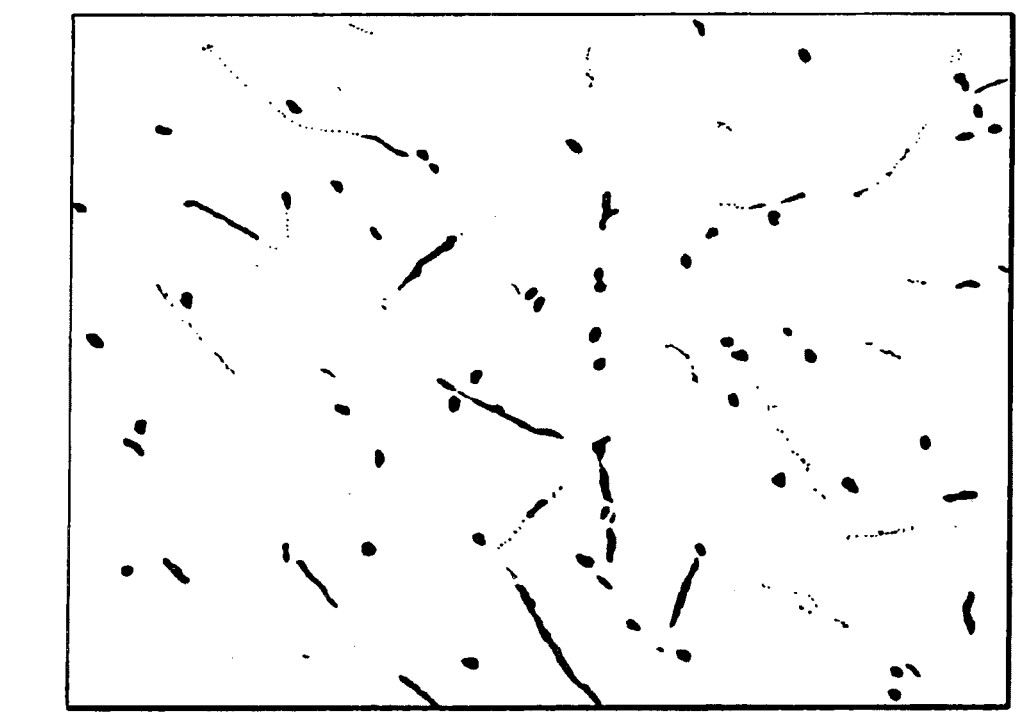

FIG. 5C.

| STATS | AREA | DIAMETER (MEAN) | PER-AREA |
|---|---|---|---|
| MIN | 4.3060365 | 2.4406509 | .00002278 |
| (OBJ. #) | 25 | 25 | 25 |
| MAX | 45.520958 | 8.1463652 | .00024088 |
| (OBJ #) | 5 | 5 | 5 |
| RANGE | 41.214920 | 5.7057142 | .00021809 |
| MEAN | 11.391845 | 3.9377844 | .00006028 |
| STD. DEV | 5.8512273 | .99111760 | .00003096 |
| SUM | 1207.5355 | 417.40515 | .00638997 |
| SAMPLES | 106 | 106 | 106 |

CLASSIFICATION

FILE VIEW

| CLASS | OBJECTS | % OBJECTS | MEAN AREA | MEAN DIA. (MEAN) |
|---|---|---|---|---|
| 1 | 54 | 50.943394 | 7.5298672 | 3.2515821 |
| 2 | 36 | 33.962265 | 12.678884 | 4.2547326 |
| 3 | 11 | 10.377358 | 17.895216 | 5.1142292 |
| 4 | 3 | 2.8301888 | 24.195824 | 6.1818633 |
| 5 | 1 | .94339621 | 29.527107 | 5.7007999 |
| 6 | 0 | 0 | 0 | 0 |
| 7 | 0 | 0 | 0 | 0 |
| 8 | 1 | .94339621 | 45.520958 | 8.1463652 |
| 9 | 0 | 0 | 0 | 0 |
| 10 | 0 | 0 | 0 | 0 |

FIG. 5D.

FIG. 6A.    1400L OUTER
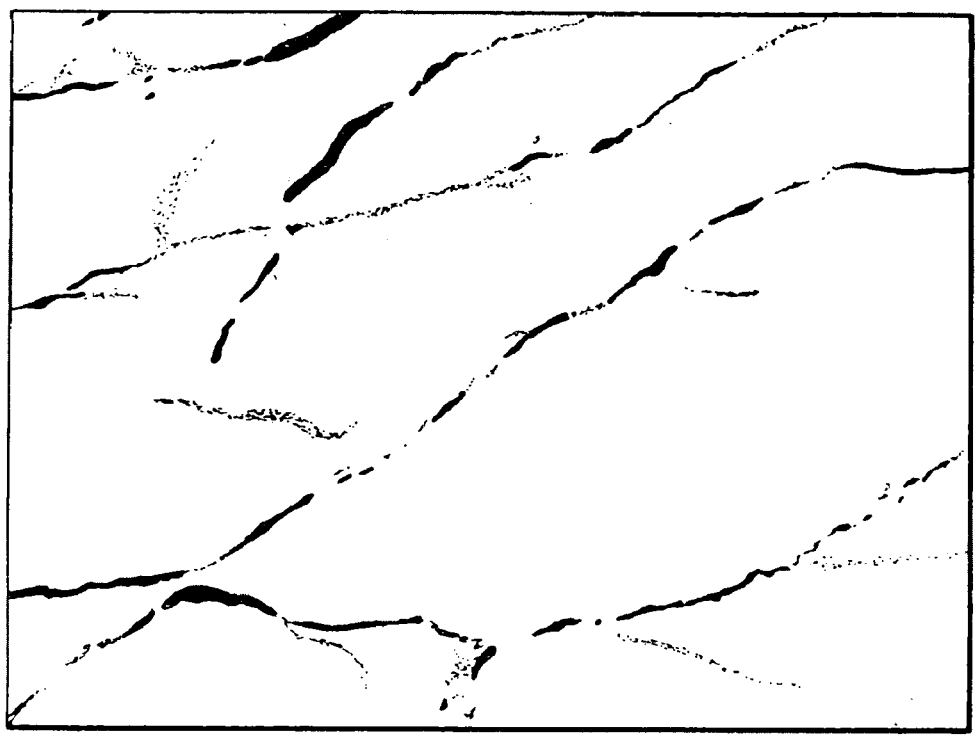
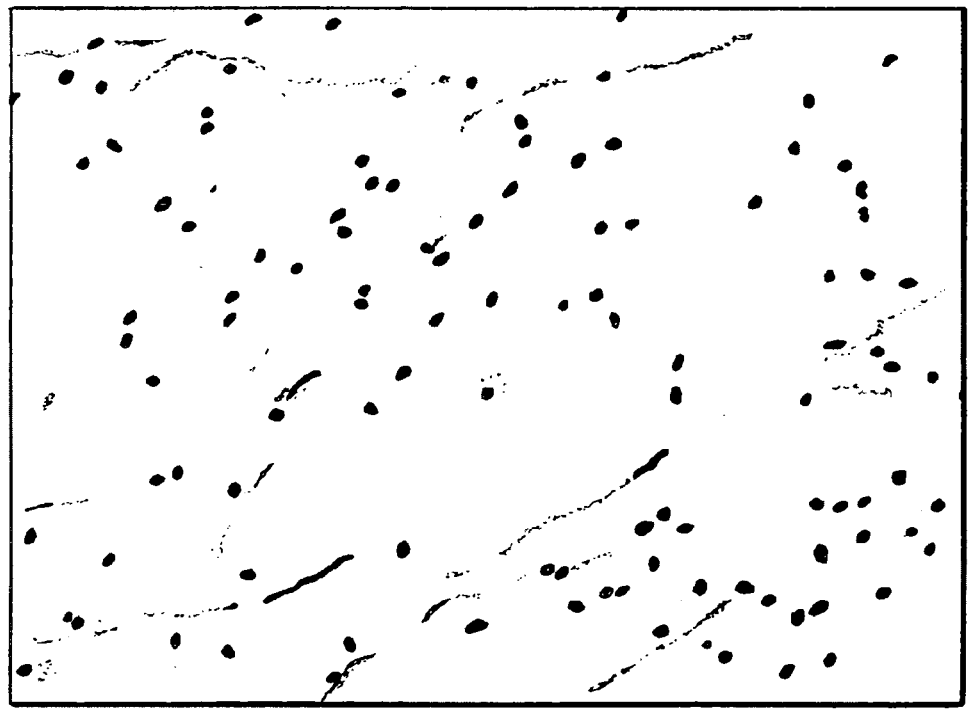
FIG. 6B.    1400 OUTER

Fig. 6C.

| STATS | AREA | DIAMETER (MEAN) | PER-AREA |
|---|---|---|---|
| MIN | 4.3060365 | 2.3132176 | .00002278 |
| (OBJ. #) | 7 | 7 | 7 |
| MAX | 65.820847 | 11.660216 | .00034830 |
| (OBJ. #) | 229 | 114 | 229 |
| RANGE | 61.514809 | 9.3469982 | .00032552 |
| MEAN | 19.463675 | 4.9798832 | .00010299 |
| STD. DEV | 10.985473 | 1.4576392 | .00005813 |
| SUM | 3737.0254 | 956.13757 | .01977539 |
| SAMPLES | 192 | 192 | 192 |

CLASSIFICATION _ □ ×

FILE VIEW

| CLASS | OBJECTS | % OBJECTS | MEAN AREA | MEAN DIA. MEAN |
|---|---|---|---|---|
| 1 | 38 | 19.7911666 | 7.0580130 | 3.1523876 |
| 2 | 39 | 20.31250 | 13.186250 | 4.3244815 |
| 3 | 51 | 26.562498 | 18.550932 | 5.0418862 |
| 4 | 32 | 16.666666 | 24.183006 | 5.6668825 |
| 5 | 11 | 5.7291665 | 29.527105 | 5.9018874 |
| 6 | 6 | 3.1250 | 34.960918 | 6.6136565 |
| 7 | 7 | 3.6458333 | 40.687653 | 7.7858882 |
| 8 | 4 | 2.0833333 | 47.058826 | 8.4272184 |
| 9 | 2 | 1.0416666 | 51.364864 | 7.6277862 |
| 10 | 1 | .52083331 | 58.349068 | 11.660216 |

Fig. 6D.

FIG. 7A.   2101L INNER
FIG. 7B.   2101L INNER
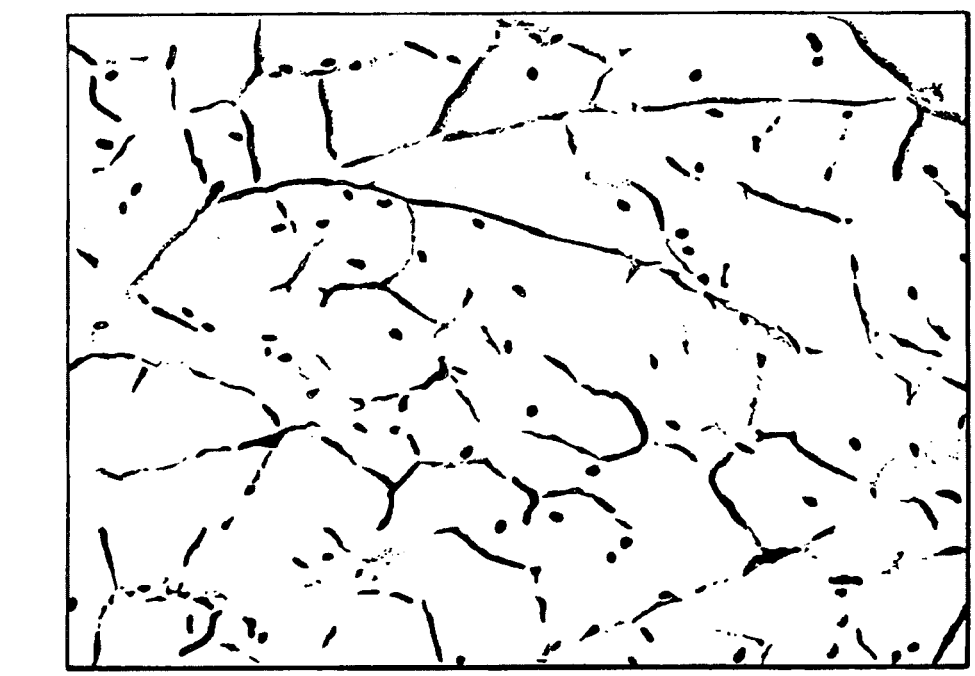

Fig. 7C.

| STATS | AREA | DIAMETER (MEAN) | PER-AREA |
|---|---|---|---|
| MIN | 4.3060360 | 2.3132174 | .00002278 |
| (OBJ. #) | 16 | 202 | 239 |
| MAX | 38.754326 | 9.5076313 | .00020507 |
| (OBJ. #) | 46 | 46 | 46 |
| RANGE | 34.448288 | 7.1944141 | .00018229 |
| MEAN | 12.421543 | 4.1032901 | .00006573 |
| STD. DEV | 6.7874541 | 1.2506217 | .00003591 |
| SUM | 2061.9761 | 681.14618 | .01091145 |
| SAMPLES | 166 | 166 | 166 |

CLASSIFICATION _ □ ×
FILE VIEW

| CLASS | OBJECTS | % OBJECTS | MEAN AREA |
|---|---|---|---|
| 1 | 80 | 48.192772 | 7.3433294 |
| 2 | 48 | 28.915663 | 12.982186 |
| 3 | 21 | 12.650602 | 17.868584 |
| 4 | 8 | 4.8192773 | 23.606304 |
| 5 | 7 | 4.2168674 | 30.518008 |
| 6 | 1 | .60240966 | 36.293732 |
| 7 | 1 | .60240966 | 38.754326 |
| 8 | 0 | 0 | 0 |
| 9 | 0 | 0 | 0 |
| 10 | 0 | 0 | 0 |

Fig. 7D.

FIG. 8A.    1400L INNER
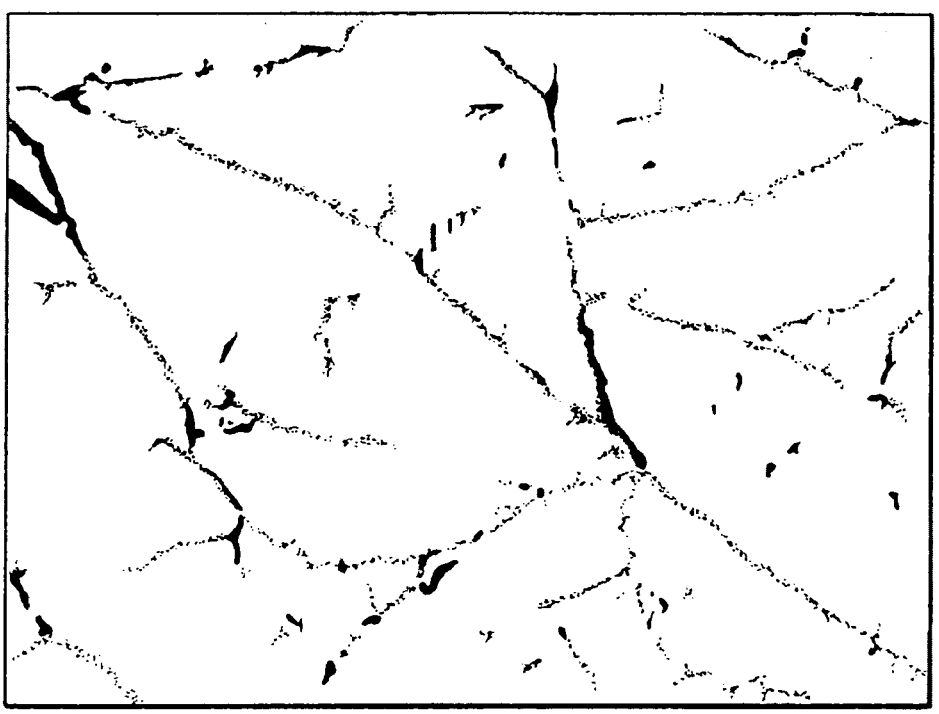
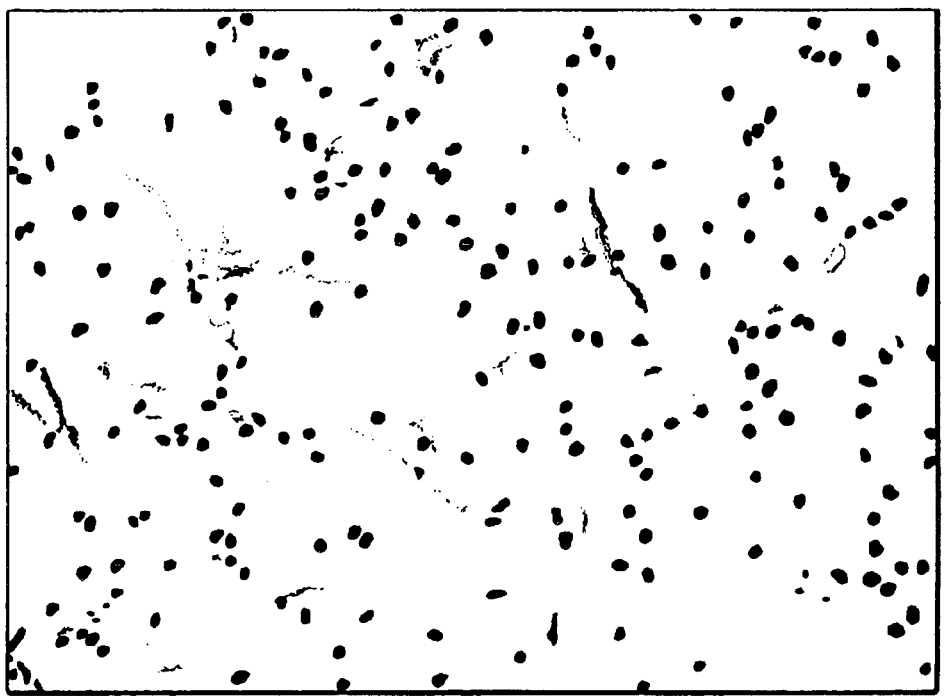
FIG. 8B.    1400L INNER

Fig. 8C.

| STATS | AREA | DIAMETER (MEAN) | PER-AREA |
|---|---|---|---|
| MIN | 4.3060365 | 2.3132176 | .00002278 |
| (OBJ.#) | 120 | 165 | 120 |
| MAX | 102.72973 | 13.133185 | .00054361 |
| (OBJ.#) | 145 | 239 | 145 |
| RANGE | 98.423691 | 10.817967 | .00052083 |
| MEAN | 18.054852 | 4.7163148 | .00009554 |
| STD.DEV | 18.469315 | 1.5011599 | .00006598 |
| SUM | 6698.3501 | 1749.7528 | .03544595 |
| SAMPLES | 371 | 371 | 371 |

CLASSIFICATION _ □ ×

FILE VIEW

| CLASS | OBJECTS | % OBJECTS | MEAN AREA | MEAN DIA [MEAN] |
|---|---|---|---|---|
| 1 | 93 | 25.067385 | 7.0642791 | 3.1215079 |
| 2 | 96 | 25.876011 | 13.059081 | 4.2343669 |
| 3 | 84 | 22.641508 | 18.183481 | 4.9487801 |
| 4 | 51 | 13.746631 | 23.761599 | 5.5594616 |
| 5 | 11 | 2.9649594 | 29.471184 | 6.0824142 |
| 6 | 8 | 2.1563342 | 35.909267 | 6.8700128 |
| 7 | 11 | 2.9649594 | 41.662304 | 7.2421188 |
| 8 | 9 | 2.4258759 | 46.546204 | 7.9324665 |
| 9 | 2 | .53908354 | 53.210308 | 8.4140301 |
| 10 | 2 | .53908354 | 57.208771 | 9.2979317 |

Fig. 8D.

TX00045 MALE RAT INJECTED GASTROCNEMIUS

TX00045 MALE RAT GASTROCNEMIUS

NUCLEI DENSITY AND NUCLEI AREA METHODS FOR DETERMINING EFFECTS OF A BOTULINUM TOXIN ON MUSCLES

CROSS REFERENCE

This application claims priority to provisional application Ser. No. 60/309,988, filed Aug. 3, 2001.

BACKGROUND

The present invention is directed to methods for determining the effects of toxins, for example *Clostridial* toxins. In particular, the present invention is directed to histological/morphological methods for determining the effects of a *botulinum* toxin.

In one embodiment, the present invention provides a method for quantitating and defining the effects of the toxins in terms of "potency." Additionally, the present invention provides a method for determining the extent of atrophy cause by the toxins.

At present the biological potency of therapeutic preparations of a *botulinum* toxin, such as a *botulinum* toxin type A is usually expressed in terms of mouse $LD_{50}$ units. Contrary to general belief, the mouse unit is not a standardized unit. It is well documented that the assay to determine the potency of *botulinum* toxin type A in mouse $LD_{50}$ units is prone to significant inter-laboratory variability (Schantz and Kautter, *J Ass of Anal Chem* 1978, 61:96–99). One study designed to standardize a *Botulinum* type A toxin assay involved 11 different laboratories (Sesardic et al, *Pharacol Toxico* 1996, 78:283–288). In this study there was found to be up to a 10-fold difference in results. This variability in mouse $LD_{50}$ is not unique to assays involving *botulinum* toxin. In fact, because of the variability of this assay, a number of regulatory agencies have abandoned requiring the routine use of $LD_{50}$ for toxicity testing for a number of chemicals, solvents, cosmetics and drugs (Pearce et al, *Toxicol App Pharm* 1994, 128:69–77; U.S. Pat. No. 5,401,243 and U.S. Pat. No. 5,183,462,).

The expanding medical importance of *botulinum* toxins has increased the need for, and placed a premium on, the precise analysis of biological activity contained in preparations of *botulinum* toxin type A for both clinical use and laboratory investigation.

Botulinum Toxin

The genus *Clostridium* has more than one hundred and twenty seven species, grouped according to their morphology and functions. The anaerobic, gram positive bacterium *Clostridium botulinum* produces a potent polypeptide neurotoxin, *botulinum* toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and attack peripheral motor neurons. Symptoms of *botulinum* toxin intoxication can progress from difficulty walking, swallowing, and speaking to paralysis of the respiratory muscles and death.

*Botulinum* toxin type A is the most lethal natural biological agent known to man. About 50 picograms of a commercially available *botulinum* toxin type A (purified neurotoxin complex)[1] is a $LD_{50}$ in mice (i.e. 1 unit). One unit of BOTOX® contains about 50 picograms (about 56 attomoles) of *botulinum* toxin type A complex. Interestingly, on a molar basis, *botulinum* toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63–84 (chapter 4) of Natural Toxins II, edited by B. R. Singh et al., Plenum Press, New York (1976) (where the stated $LD_{50}$ of *botulinum* toxin type A of 0.3 ng equals 1 U is corrected for the fact that about 0.05 ng of BOTOX® equals 1 unit). One unit (U) of *botulinum* toxin is defined as the $LD_{50}$ upon intraperitoneal injection into female Swiss Webster mice weighing 18 to 20 grams each.

[1] Available from Allergan, Inc., of Irvine, Calif. under the tradename BOTOX® in 100 unit vials)

Seven *botulinum* neurotoxins have been characterized, these being respectively *botulinum* neurotoxin serotypes A, B, $C_1$, D, E, F and G each of which is distinguished by neutralization with type-specific antibodies. The different serotypes of *botulinum* toxin can vary in the animal species that they affect and in the severity and duration of the paralysis they evoke. *Botulinum* toxin apparently binds with high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of *botulinum* toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of *botulinum* toxin activity appears to involve reduction of the disulfide bond joining the heavy chain, H chain, and the light chain, L chain. The entire toxic activity of *botulinum* and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, *botulinum* toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. *Botulinum* toxin serotype A and E cleave SNAP-25. *Botulinum* toxin serotype $C_1$ was originally thought to cleave syntaxin, but was found to cleave syntaxin and SNAP-25. Each of the *botulinum* toxins specifically cleaves a different bond, except *botulinum* toxin type B (and tetanus toxin) which cleave the same bond.

Botulinum toxins have been used in clinical settings for the treatment of neuromuscular disorders characterized by hyperactive skeletal muscles. A botulinum toxin type A complex (BOTOX®) has been approved by the U.S. Food and Drug Administration for the treatment of blepharospasm, strabismus and hemifacial spasm, cervical dystonia and treatment of glabellar wrinkles. A type B botulinum toxin (MYOBLOCT™) has also been approved by the FDA for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within a day or a few hours after injection. The typical duration of symptomatic relief from a single intramuscular injection of botulinum toxin type A averages about three to four months.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. Biochem, J 1;339 (pt 1):159–65:1999, and Mov Disord, 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51(2);522–527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165;675–681:1897. Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine*, Toxicon 35(9);1373–1412 at 1393; Bigalke H., et al., *Botulinum A Neurotoxin Inhibits Non-Cholinergic Synaptic Transmission in Mouse Spinal Cord Neurons in Culture*, Brain Research 360;318–324:1985; Habermann E., *Inhibition by Tetanus and Botulinum A Toxin of the release of [$^3$H]Noradrenaline and [$^3$H]GABA From Rat Brain Homogenate*, Experientia 44;224–226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244–251:1981, and; Jankovic J. et al., *Therapy With Botulinum Toxin*, Marcel Dekker, Inc., (1994), page 5.

Botulinum toxin type A can be obtained by establishing and growing cultures of Clostridium botulinum in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and non-proteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A.

High quality crystalline botulinum toxin type A can be produced from the Hall A strain of Clostridium botulinum with characteristics of $\geq 3 \times 10^7$ U/mg, an $A_{260}/A_{278}$ of less than 0.60 and a distinct pattern of banding on gel electrophoresis. The known Shantz process can be used to obtain crystalline botulinum toxin type A, as set forth in Shantz, E. J., et al, *Properties and use of Botulinum toxin and Other Microbial Neurotoxins in Medicine*, Microbiol Rev. 56;80–99:1992. Generally, the botulinum toxin type A complex can be isolated and purified from an anaerobic fermentation by cultivating Clostridium botulinum type A in a suitable medium. The known process can also be used, upon separation out of the non-toxin proteins, to obtain pure botulinum toxins, such as for example: purified botulinum toxin type A with an approximately 150 kD molecular weight with a specific potency of 1–2×10$^8$ LD$_{50}$ U/mg or greater; purified *botulinum* toxin type B with an approximately 156 kD molecular weight with a specific potency of $1-2\times10^8$ LD$_{50}$ U/mg or greater, and; purified *botulinum* toxin type F with an approximately 155 kD molecular weight with a specific potency of $1-2\times10^7$ LD$_{50}$ U/mg or greater.

*Botulinum* toxins and/or *botulinum* toxin complexes can be obtained from Allergan Inc (Irvine, Calif.), Ipsen Beaufour (France), Elan Pharmaceuticals (Ireland), List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo.

Though somewhat labile, pure *botulinum* toxin can be used to prepare a pharmaceutical composition and like the *botulinum* toxin complexes, such as the toxin type A complex, is susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the *botulinum* toxins (which are intracellular peptidases) is dependent, at least in part, upon their three dimensional conformation. Thus, *botulinum* toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can be stabilized with a stabilizing agent such as albumin and gelatin.

A commercially available *botulinum* toxin containing pharmaceutical composition is sold under the trademark BOTOX® (available from Allergan, Inc., of Irvine, Calif.). BOTOX® consists of a purified *botulinum* toxin type A complex, albumin and sodium chloride packaged in sterile, vacuum-dried form. The *botulinum* toxin type A is made from a culture of the Hall strain of *Clostridium botulinum* grown in a medium containing N-Z amine and yeast extract. The *botulinum* toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below $-5°$ C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about $2°$ C. to about $8°$ C. Reconstituted, refrigerated BOTOX® has been reported to retain its potency for at least about four weeks. *Dermatol Surg* 1996 Jan. 22(1):39–43.

It has been reported that *botulinum* toxin type A has been used in clinical settings as follows:

(1) about 75–125 units of BOTOX® per intramuscular injection (multiple muscles) to treat cervical dystonia;

(2) 5–10 units of BOTOX® per intramuscular injection to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U (b) flexor digitorum sublimus: 7.5 U to 30 U (c) flexor carpi ulnaris: 10 U to 40 U (d) flexor carpi radialis: 15 U to 60 U (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular *botulinum* toxin has been used in the treatment of tremor in patient's with Parkinson's disease, although it has been reported that results have not been impressive. Marjama-Jyons, J., et al., *Tremor-Predominant Parkinson's Disease*, Drugs & Aging 16(4); 273–278:2000.

It is known that *botulinum* toxin type A can have an efficacy for up to 12 months (*European J. Neurology* 6 (Supp 4): S111–S1150:1999), and in some circumstances for as long as 27 months. *The Laryngoscope* 109:1344–1346:1999. However, the usual duration of an intramuscular injection of Botox® is typically about 3 to 4 months. The success of *botulinum* toxin type A to treat a variety of clinical conditions has led to interest in other *botulinum* toxin serotypes. See e.g. *Eur J Neurol November* 1999;6(Suppl 4):S3—S10.

The tetanus neurotoxin acts mainly in the central nervous system, while *botulinum* neurotoxin acts at the neuromuscular junction; both act by inhibiting acetylcholine release from the axon of the affected neuron into the synapse, resulting in paralysis. The effect of intoxication on the affected neuron is long-lasting and until recently has been thought to be irreversible. The tetanus neurotoxin is known to exist in one immunologically distinct serotype.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic and most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of the heart by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and insulin, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

It would be advantageous to provide a more precise measurement of toxin activity based on a non-lethal exposure of a botulinum toxin, such as a botulinum toxin type A, to a mammal such as a rat. This invention provides for a better method of determining potency of a toxin.

DRAWINGS

FIG. 3 shows that the nuclei number (within a discrete area) in a muscle is inversely proportional to the muscle mass.

FIG. 4 shows that an increase in nuclei area corresponds to lower muscle mass.

FIGS. 5, 6, 7 and 8 show a computer recognition and analysis of nuclei on muscle slides. The muscles of FIGS. 5 and 7 are not treated with botulinum toxin. The muscles of FIGS. 6 and 8 are treated with botulinum toxin.

Figure 9:
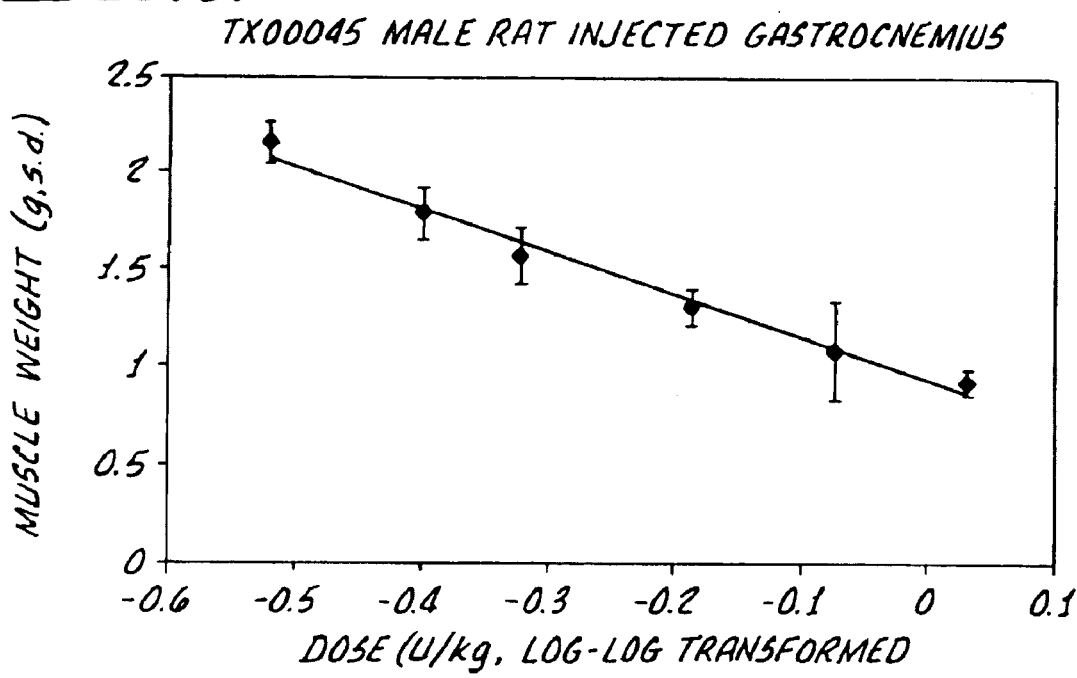

FIG. 9 shows the relationship between muscle weight and dose of botulinum toxin injected.

Figure 10:
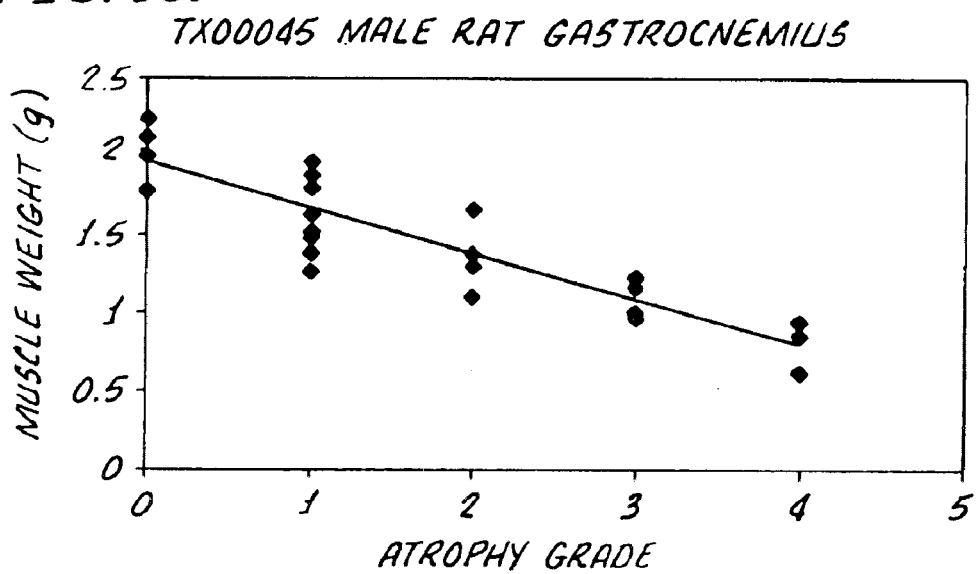

FIG. 10 shows the relationship of muscle weight and atrophy grade.

Figure 11:
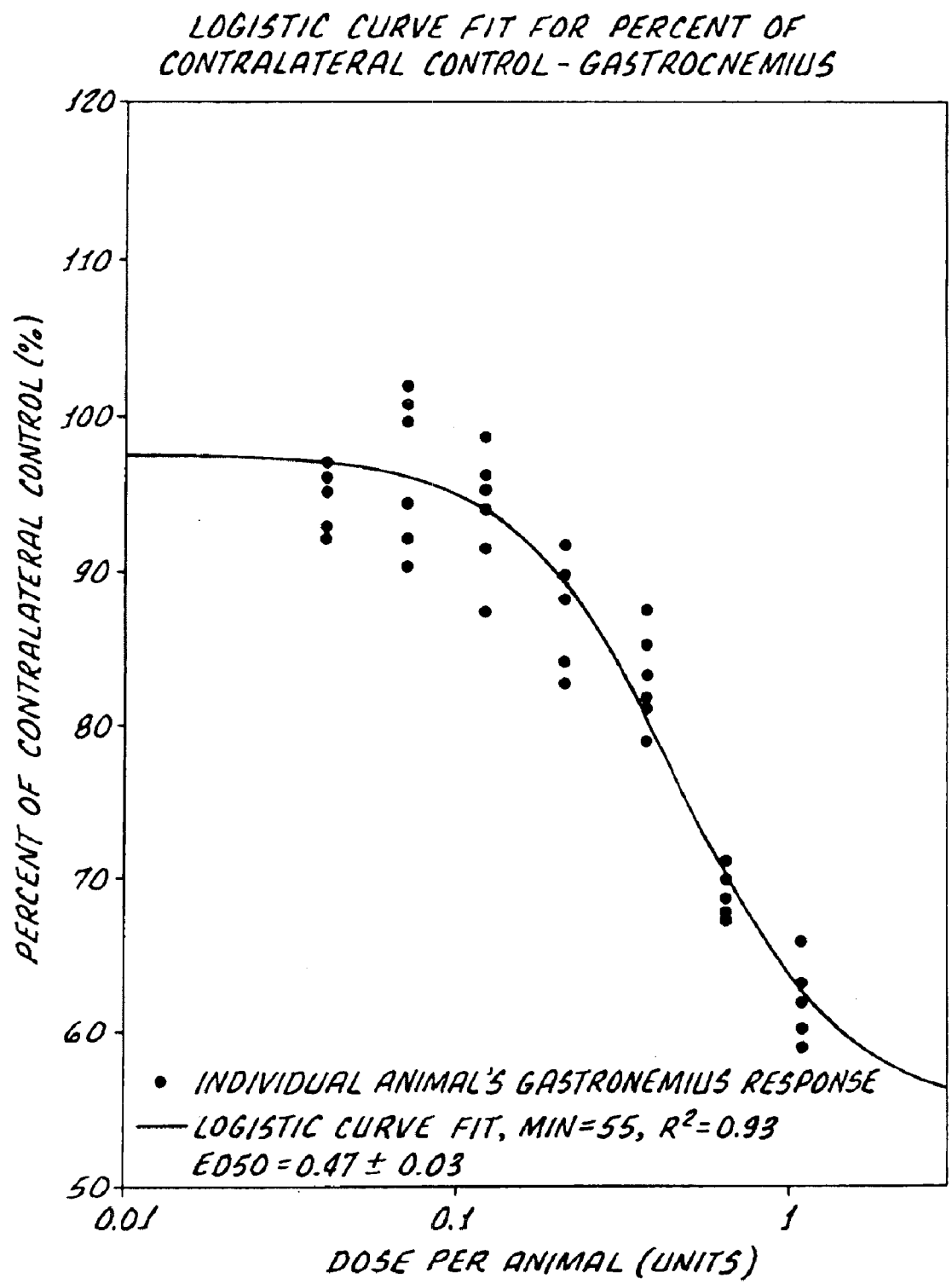

FIG. 11 is a graph which shows the result of an experiment where the left gastrocnemius muscle of different rats was injected with varying amounts of a botulinum toxin type A. The y axis shows the ratio (as a percent) of the weight of the toxin injected left gastrocnemius muscle of the rat to the weight of the uninjected right gastrocnemius muscle of the same rat. The x axis shows the amount in units of the botulinum toxin type A that was injected into the left gastrocnemius muscle.

Figure 12:
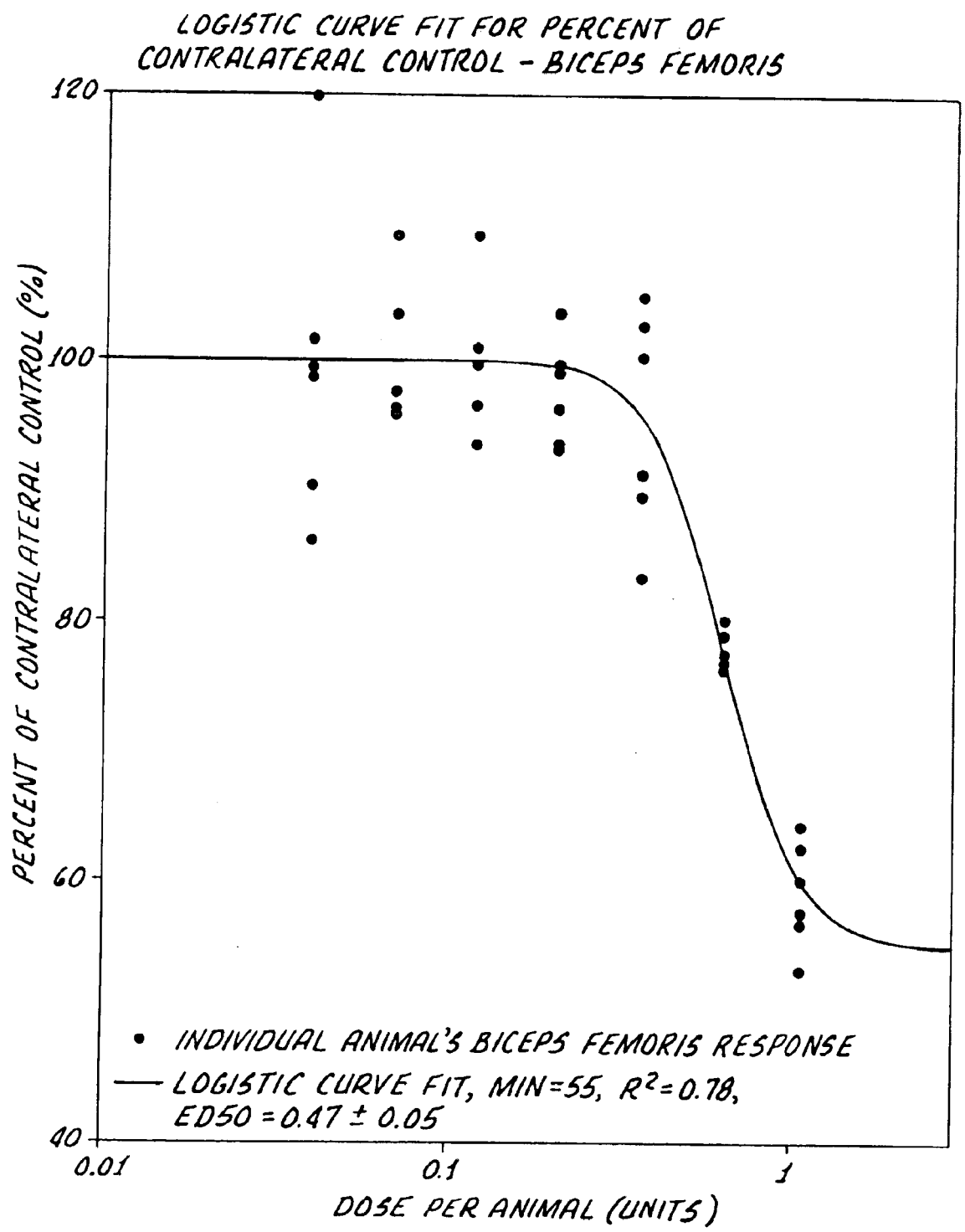

FIG. 12 is a graph which shows the result of an experiment where the left gastrocnemius muscle of different rats was injected with varying amounts of a botulinum toxin type A. The y axis shows the ratio (as a percent) of the weight of the uninjected left biceps femoris muscle (which is adjacent to the toxin injected left gastrocnemius muscle of the rat) to the weight of the uninjected right biceps femoris muscle of the same rat. The x axis shows the amount in units of the botulinum toxin type A that was injected into the left gastrocnemius muscle.

Figure 13:
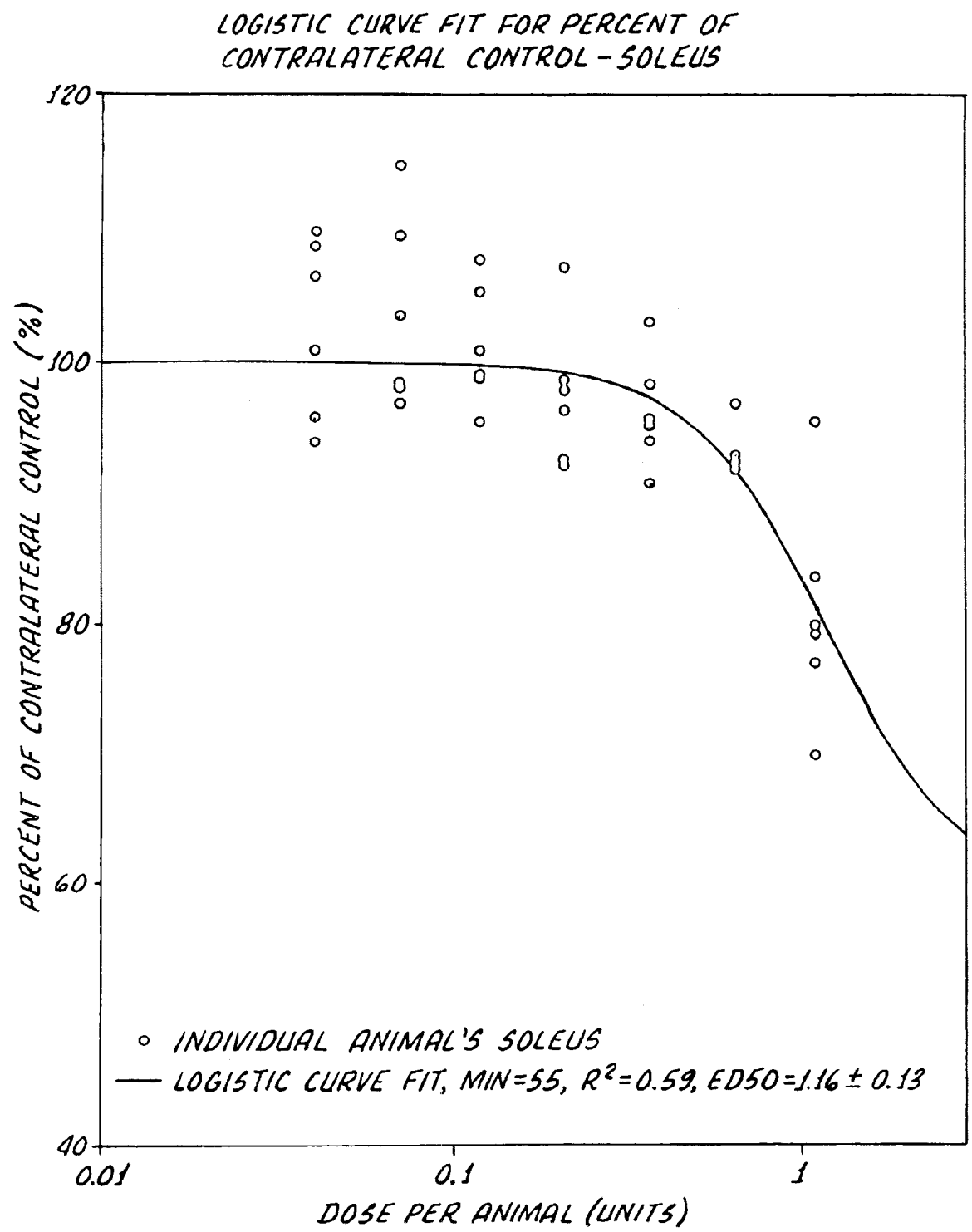

FIG. 13 is a graph which shows the result of an experiment where the left gastrocnemius muscle of different rats was injected with varying amounts of a botulinum toxin type A. The y axis shows the ratio (as a percent) of the weight of the uninjected left soleus muscle (which is adjacent to the toxin injected left gastrocnemius muscle of the rat) to the weight of the uninjected right soleus muscle of the same rat. The x axis shows the amount in units of the botulinum toxin type A that was injected into the left gastrocnemius muscle.

DEFINITIONS

"Potency" a measure of a mass of a certain chemical, e.g. a toxin, to induce a certain degree of physiological or chemical effect. For example, potency of a botulinum toxin means the extent of or the duration of inhibition of acetylcholine release from a target tissue. Alternatively, a potency of a botulinum toxin means the extent that a certain dose of toxin causes a certain nuclear index changes.

"Atrophy" is a reduction in muscle mass. The degree of muscle atrophy can be measured by a change in percentage of muscle mass, circumference and/or length.

"Nuclear index" means number of nuclei per area of muscle (nuclei density), the sum of the area of the individual nuclei within a field (nuclei area), and/or the level of electrically coupled factors.

"Electrically coupled factors" may be proteins (for example, transcription factors) or nucleic acid sequences [e.g. mRNA] of MyoD, Myogenin, Myr-5, MRF4, sTnI, and/or tTnI.

"Muscle Weight" is the mass of the muscle.

"Atrophy grade" is the percentage of atrophy of a muscle fiber, relative to an analogous control muscle fiber, which may be determine via visual inspection. Each "grade" corresponds to about 25% reduction in muscle mass relative to the control.

Our invention encompasses a method for determining an effect of a *Clostridial* toxin, the method comprising the step of administering the *Clostridial* toxin to a muscle of a mammal, and determining a nuclear index of the injected muscle. The *Clostridial* toxin can be selected from the group consisting of *Clostridial beratti, Clostridia butyricum, Clostridial tetani* bacterium and *Clostridial botulinum*. The *Clostridial* toxin can be selected from the group consisting of *botulinum* toxin types A, B, $C_1$, D, E, F, G and mixtures thereof and is preferably a *botulinum* toxin type A.

The effect of a *Clostridial* toxin can be determined by determining a potency or diffusion of the toxin and this can be carried out by determining the nuclear index which comprises measuring nuclei density. The step of determining the nuclear index can comprise measuring nuclei area. Additionally, the step of determining the nuclear index comprises measuring the nuclei density and nuclei area. The step of determining the nuclear index can comprise measuring the level of electrically coupled factors. The step of determining the nuclear index can comprise measuring the level of electrically coupled factors and nuclei density. The step of determining the nuclear index can comprise measuring the level of electrically coupled factors and nuclei area.

Additionally, the step of determining the nuclear index can comprise measuring the level of electrically coupled factors, nuclei density, and nuclei area. The electrically coupled factors can comprise proteins. The electrically coupled factors can comprise nucleic acid sequences. The electrically coupled factors can comprise the mRNAs of MyoD, Myogenin, Myr-5, MRF4, sTnI, tTnI.

A further embodiment of our invention is a method for determining muscle atrophy induced by the administration of a *Clostridium* toxin, the method comprises the step of comparing a nuclear index of the muscle injected with *Clostridial* toxin to that of a muscle which is not injected with *Clostridial* toxin. The nuclear index can be measurement of the level of electrically coupled factors, nuclei density, and nuclei area.

Our invention also encompasses a method for determining an effect of a *Clostridial* toxin, the method comprising the step of administering the *Clostridial* toxin to a muscle of a mammal, and determining an atrophy of a muscle. The effect of a *Clostridial* toxin can be determined by determining a potency of the toxin. The step of determining atrophy can comprises measuring a reduction in muscle mass of either the muscle injected with the toxin or of an adjacent muscle.

A detailed embodiment of our invention include a method for determining an effect of a *Clostridial* toxin, the method comprising the step of administering the *Clostridial* toxin to a muscle of a mammal, and determining an atrophy of a muscle by comparing a muscle mass of the muscle injected with a *Clostridial* toxin to that of a muscle which is not injected with a *Clostridial* toxin.

DESCRIPTION

The present invention is, in part, based upon the discovery that a nuclear index of a muscle may be employed to assess toxin potency and muscle atrophy.

I. Methods of Determining the Potency of a Toxin

In a broad embodiment, the method for determining the effect of a *Clostridial* toxin comprises the step of administering the toxin to a muscle of a mammal and determining the nuclear index of the injected muscle. The effect of a toxin may be defined by its potency. In one embodiment, the present invention provides for a method of determining the potency of a *Clostridial* toxin on a muscle. "Mammals" as used herein include, for example, human beings, rats, rabbits, mice and dogs.

The *Clostridial* toxin may be *Clostridial beratti, Clostridia butyricum, Clostridial botulinum*, and *Clostridial tetani* bacterium. In a preferred embodiment the method measures the potency of *Botulinum* toxins, for example *Botulinum* toxin A, B, $C_1$, D, E, F, G, and mixtures thereof.

The step of determining the nuclear index includes a measuring the number of nuclei per area of tissue, a measuring the sum of the individual area of the nuclei over an area of tissue, and/or a measuring the level of electrically coupled factors. Examples of electrically coupled factors include mRNAs of MyoD, Myogenin, Myr-5, MRF4, sTnI and/or tTnI. See Voytik et al., Developmental Dynamics 198:214–224 (1993).

It is discovered that the number and sizes of the nuclei, in particular the sarcolemma nuclei, increases with an increasing dose of toxin, for example *botulinum* toxin type A, that is administered to a muscle. Also, the level of electrically coupled factors in the muscle changes, for example increase or decrease, with an increasing dose of toxin. As such, a dose response curve may be constructed to determine a potency of a toxin. The potency as determined by this method is termed $ED_{50}$ (effective dose at 50%). It is believed that the potency as determined by this method is more accurate and more reliable than the traditional $LD_{50}$, as described above.

Figure 1:
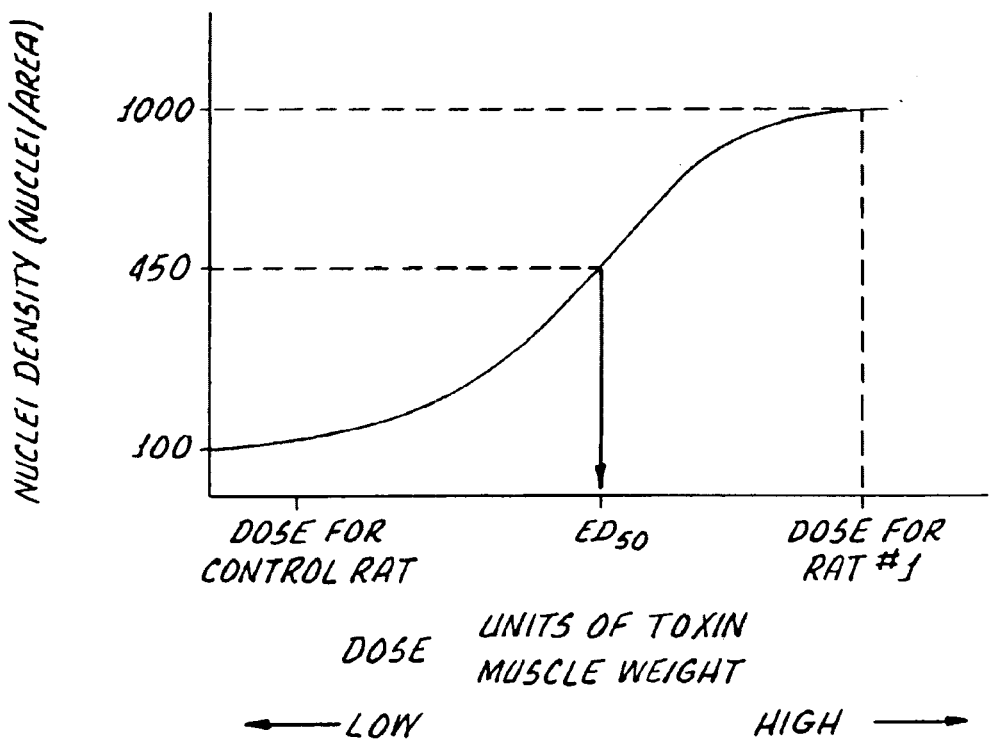
FIG. 1 illustrates a sample dose response curve constructed from plotting the nuclear index against the dose of toxin, for example botulinum toxin.

FIG. 1 shows an exemplary dose response curve constructed from plotting the nuclear density against the increasing dose of toxin, for example *botulinum* toxin. The $ED_{50}$ is the concentration which correspond to the halfway point between the lowest and the highest nuclei density. For example, the $ED_{50}$ of FIG. 1 is the dose of *botulinum* toxin corresponding to 450 nuclei/unit area, which is half of 1000 and 100 nuclei/unit area.

In another embodiment, the nuclei area may be plotted against the varying dose of a *Clostridial* toxin, preferably *botulinum* toxin, to obtain an $ED_{50}$.

In one embodiment, standard nuclei staining techniques may be employed to identify the nuclei for purposes of counting the number of nuclei or determining the sum of their area. Various non-limiting examples of staining techniques are listed herein below.

After staining the nuclei, the nuclear index, for example the number of nuclei per area of muscle tissue or the sum of the individual nuclei over an area of muscle tissue, may be obtained with an assistance of a computer. Various computer programs known in the art may be employed in accordance with this invention. In one embodiment, these programs are used to direct a computer to recognize certain patterns, preferably that of a nucleus, on a stained muscle slide. After identifying the nuclei, the program will further direct the computer to sort the nuclei according to size or volume and group them into bins of similar sizes or volume. An example of such program which may be used in accordance with this invention includes Image Pro 4.1 (MediaCybernetics, Inc.).

FIG. 5B shows a computer recognition image of the nuclei of a muscle slide. FIG. 5D shows that there are ten bins. Bin #1 has 54 objects (or nuclei) having the mean area of 7.5 um. FIG. 5C shows that there are a total of 106 nuclei.

FIG. 6 shows that when an analogous muscle is treated with *botulinum* toxin, the nuclei are larger, more plump and more numerous. For example, FIG. 6D shows that there are nuclei as large as 58 um. Furthermore, FIG. 6C shows that the number of nuclei increases to 192. FIG. 7 relates to FIG. 8 as FIG. 5 relates to FIG. 6.

EXAMPLE 1

Determining the Potency of *Botulinum* Toxin with Nuclei Area

A batch of *botulinum* toxin type A is prepared by a standard methodology. A serial dilution of the toxin is done by a standard methodology. The stock solution of the toxin is set at an approximate concentration of 50 picograms of *botulinum* toxin type A/microliter. Five fold dilutions are done with the final serial dilution factors ranging from 1.0 (stock solution) to $1.0 \times 10^{-4}$. In addition, rats, one for each serial dilution, are prepared for a potency assay. 1.0 microliter of each of the nine dilutions is injected into the gastrocnemius muscle of each of the rats as follows:
Rat No. 1, dilution factor=1.0
Rat No. 2, dilution factor=$5.0 \times 10^{-1}$
Rat No. 3, dilution factor=$1.0 \times 10^{-1}$
Rat No. 4, dilution factor=$5.0 \times 10^{-2}$
Rat No. 5, dilution factor=$1.0 \times 10^{-2}$
Rat No. 6, dilution factor=$5.0 \times 10^{-3}$
Rat No. 7, dilution factor=$1.0 \times 10^{-3}$
Rat No. 8, dilution factor=$5.0 \times 10^{-4}$
Rat No. 9, dilution factor=$1.0 \times 10^{-4}$
Rat No. 10 (Control Rat), sterile saline/no toxin After 14 days, the rats are sacrificed. The gastrocnemius muscle of each rat is removed, prepared and mounted on slides for analysis. The nuclei density (or nuclei area) of the Rat muscle is determined.

The nuclei density is plotted against the dose injected into the muscles of the rats. The $ED_{50}$ is determined from the plot. See FIG. 1.

EXAMPLE 2

Methods for Staining Muscle Cell Nucleus

Techniques of staining for the nuclei of muscles are well known. These include the Hematoxylin and Eosin (H&E), Propidium Iodine, DAPI, and Hoechst. See Manual of Histologic Staining Methods of the Armed Forces Institute of Pathology (Third Edition). American Registry of Pathology (Luna, Lee G., HT(ASCP) (editor)), McGraw Hill Publishers, New York 1960. Wang and Gerdes, J Mol Cell Cardiol 29, 1553–1565 (1997). Lim and Alvarez-Buylla, Proc. Natl. Acad. Sci.USA 96, 7526–7531, (1999).
Hematoxylin & Eosin The staining procedure involves using deparaffinized sections, after which they are rehydrated. If the sections are Zenker-fixed, remove the mercuric chloride crystals with iodine and clear with sodium thiosulphate (hypo). Next, add Mayer's hematoxylin for 15 minutes. Wash in running tap water for 20 minutes.

Counterstain with eosin from 15 seconds to 2 minutes depending on the age of the eosin, and the depth of the counterstain desired. For even staining results, dip slides several times before allowing them to set in the eosin for the desired time. Then dehydrate in 95% and absolute alcohols, two changes of 2 minutes each or until excess eosin is removed. Check under a microscope. Clear in xylene, two changes of 2 minutes each, and mount in Permount or Histoclad.

The stains appear as follows: the nuclei appear blue, with some metachromasia Cytoplasm and various shades of pink identifying different tissue components The adhesives used to attach sections onto the slides (gelatin, egg albumen) sometimes stain, in areas around the section, with Mayor's hematoxylin. This gives the slides a slightly dark appearance but in no way affects the nuclear staining. To remedy this, use 10–12% glacial acetic acid in 95% alcohol, to "clean" the slides after Mayor's hematoxylin. Following with a few dips in saturated aqueous lithium carbonate, the nuclei become blue immediately. This is optional, for the 20-minute wash in running water is sufficient to blue the nuclei.

In one embodiment, the Sakura Finetek DRS-60 Stainer may be used in accordance with the present invention.
Staining Nucleus with Propidium Iodide (PI)

The muscle cells may be fixed with 4% PFA for 30 min at room temperature. Then the cells are to be washed 3 times, 5 min with PBS. Next, incubate cells for 5 min at room temperature in 1.25 ug/ml propidium idodide (Sigma Chemical Co., St. Louis, Mo.).
Staining Nucleus with DAPI First, repeat the three steps from staining with Pi except the counterstain is done with DAPI. DAPI (4'-6-Diamidino-2-phenylindole-2HCl') (Serva) Stock solution is prepared with 0.2 mg/ml of distilled water.

The staining solutions are prepared with 0.2–0.4 $\mu$g/ml of buffer PBS.

Flood with DAPI solution, cover with coverslip and incubate in the dark at room temp. for 5–15 mins. Then rinse briefly with PBS.
Staining Nucleus with Hoechst 33258

Fix the muscle cells with 4% PFA for 30 min at room temperature. Wash the cells 3 times for 5 min with PBS. Then incubate the cells for 5 min at room temperature in 0.5 ug/ml Hoechst 33258. Wash briefly with PBS.

EXAMPLE 3

Isolating the mRNAs of Electrically Coupled Factors

To determine the relative abundance of mRNAs specific for slow troponin 1 (sTNl), fast troponin 1 (fTnl), and each muscle regulatory factor (MRF), standard RNA isolation and Northern hybridization procedures are performed. Total RNA is isolated from frozen muscle samples by acid guanidinium isothiocyanate/phenol/chloroform extraction followed by isopropanol precipitation (Chomczynski and Sacchi, 1987). The RNA is obtained from mammals, for example rats or humans.

Analogous muscles of 4 to 6 different subjects is pooled. Total muscle RNA is isolated in a similar fashion and serves as a negative control. RNA samples (20 ug) are fractionated by electrophoresis through 1% agarose/formaldehyde gels (Lehrach et al., 1977), transferred to Nytran (Schleicher and Schuell, Keene, N.H.), and immobilized by UV crosslinking. Random primed cDNA probes (specific activity $\geq 1 \times 10*8$ cpm/ug) then they are hybridized to the membranes at 65C in 6×SSC (1×SSC consists of 0.15 M Tris-Cl, pH 7.5, 5× Denhardt's solution, 2 mM EDTA, pH 8.0, 0.5% SDS) and 100 ug/ml denatured salmon sperm DNA. The cDNA probes used in this study include rat MRF4 (Davis et al., 1987), rat myogenin (Wright, et al., 1989), human Myf-5 (Braun et al., 1989), and mouse fast and slow troponin 1 (Koppe et al., 1989). Following hybridization, all membranes are washed for 1 hr at 65C in 0.1×SSC, 0.2% SDS, except for those probed with Myf-5 and MyoD which are washed in 0.5×SSC, 0.2% SDS. In some instances, the hybridized probes are removed from the filters by washing the membranes in 5 mM Tris-Cl, pH 7.5, 0.2 mM EDTA, pH 8.0, 0.05% pyrophosphate, and 0.1× Denhardt's at 65C for 1 to 2 hr. The filters are then rinsed briefly in 2×SSPE (1×SSPE consists of 0.15 M NaCl, 10 mM sodium phosphate, 1 mM EDTA, pH 7.4) after which additional hybridizations are performed. To quantitate autoradiograms obtained form Northern hybridization analyses, a densitometric evaluation is performed using an Ultrascan XL Laser Densitometer (Pharmacia LKB Biotechnology, Piscataway, N.J.). Multiple autoradiogram exposures are scanned to insure that band densities remained within the linear response range of the film.

II. Methods of Using Nuclear Index and/or Muscle Atrophy to Determine Toxin Potency and Diffusion The present invention provides for a faster, easier, more sensitive and more accurate method for assessing muscle atrophy as a parameter for determining toxin potency and/or diffusion. The method comprises the step of comparing a nuclear index of the muscle suspected of being atrophied to that of a muscle which is normal. Preferably, the present invention provides for a method of assessing muscle atrophy due to the effects of *Clostridium* toxin by comparing a nuclear index of the muscle injected with *Clostridial* toxin to that of an analogous muscle which is not injected with *Clostridial* toxin.

Figure 2:
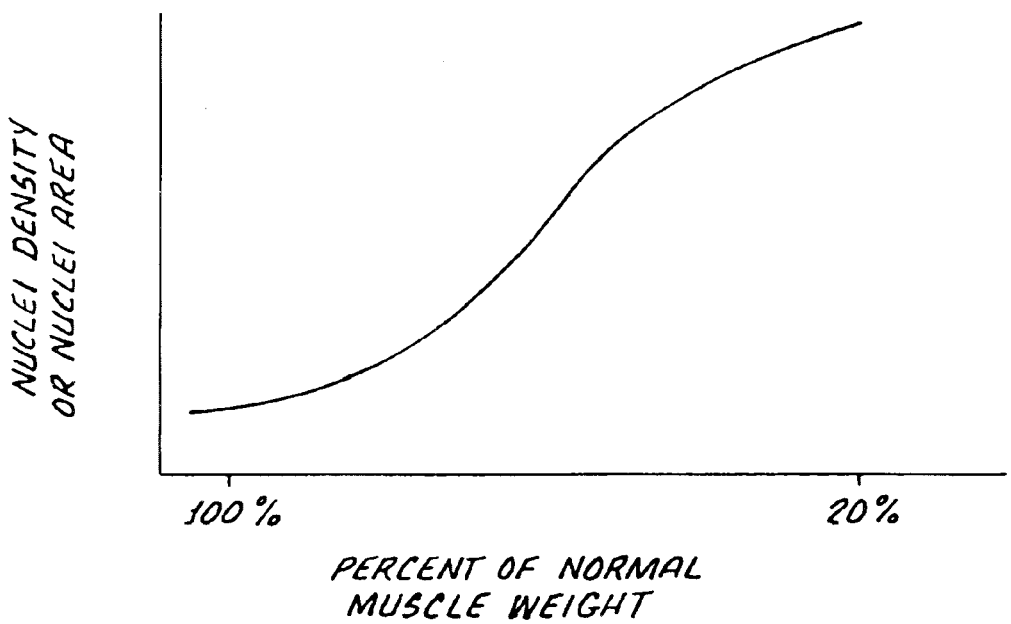
FIG. 2 shows that the nuclei area (within a discrete area) in a muscle is inversely proportional to the muscle mass.

It is presently discovered that the nuclear index varies proportionately with the degree of muscle atrophy. For example, FIGS. 2 (and 3) shows that the nuclei area (and nuclei number) in a muscle is inversely proportional to the muscle mass. FIG. 4 shows that an increase in nuclei area corresponds to lower muscle mass. Thus, the extent of changes in the nuclear index reveals the extent of muscle atrophy. For example, a small increase in nuclei density after an administration of *botulinum* toxin is indicative that the muscle has not atrophied much. Whereas, a large increase in nuclei is indicative that the muscle has significantly atrophied.

In one embodiment, the extent of changes in nuclear index, which is change in muscle weight and fiber diameter, of the various injected muscle will demonstrate the inherent activity of a toxin, for example *botulinum* toxin, at a therapeutically relevant site. In addition, the diffusion potential of the toxin protein in a given formulation may be quantitated within the same mammals by the extent of muscle atrophy of the muscles (of various fiber types) peripheral to the injection site.

EXAMPLE 4

Muscle Atrophy Assay

The extent of muscle atrophy in response to *botulinum* toxin treatment in terms of decreases in muscle weight and muscle fiber diameter can be determined using the methods of this invention.

Adult rats are injected intramuscularly with a single dose of *botulinum* toxin into the midbelly area (location of motor endplate) of each rat's left gastrocnemius muscle. Doses are at a low level of 0 to 2.5 U per rat (up to ~10 U/kg) to minimize systemic toxicity which can be a confounding factor for the evaluation of local pharmacologic effects. At a selected time point within two weeks of dosing, several muscles from the injected hind leg will be collected for gravimetric and histopathologic evaluations. Muscle collection includes muscles of different fiber types: the injected muscle (gastrocnemius), two muscles immediately adjacent to the injection site (biceps femoris and soleus), and two muscles further away from the injection site (peroneus and tibialis).

Muscle weight changes may be normalized against each rat's body weight. The extent of muscle weight decreases may be expressed by comparison with muscles from each rat's uninjected, contralateral leg or with placebo injected controls.

Histopathologic evaluation may involve qualitative assessment on a standard scale (grade 1 to 5, corresponding to minimal to maximal reduction in fiber diameter) or quantitative measurement with computer-assisted morphometric evaluation. See FIGS. 9 and 10.

EXAMPLE 5

Muscle Weight as a Measure of *Botulinum* Toxin Type A Potency and Diffusion

Female Sprague Dawley derived rats (young adult, about 250 grams in body weight) were injected with a single dose of a *botulinum* toxin type A complex (BOTOX®) into only the left gastrocnemius muscle. The individual doses injected into separate rat left gastrocnemius muscles were 0.04 unit, 0.07 unit, 0.12 unit, 0.21 unit, 0.37 unit, 0.65 unit and 1.1 units. Adjacent to the toxin injected left gastrocnemius muscle were the uninjected left biceps femoris and the uninjected left soleus muscles. The right gastronemius muscle, the right biceps femoris muscle and the right soleus muscle of each rat were not injected and were therefore retained as controls. Muscles from both (injected and uninjected) left and right hindlegs (gastrocnemius muscle), as well as the uninjected left and uninjected right biceps femoris and soleus muscles, were extracted at 14 days after dosing of the left gastronemius muscles and then weighed.

FIG. 11 shows the result of this experiment where the left gastrocnemius muscle of different rats was injected with varying amounts of a *botulinum* toxin type A. The y axis shows the ratio (as a percent) of the weight of the toxin injected left gastrocnemius muscle of the rat to the weight of the uninjected right gastrocnemius muscle of the same rat. The x axis shows the amount in units of the *botulinum* toxin type A that was injected into the left gastrocnemius muscle.

FIG. 12 shows the result of this experiment where the left gastrocnemius muscle of different rats was injected with varying amounts of a *botulinum* toxin type A. The y axis shows the ratio (as a percent) of the weight of the uninjected left biceps femoris muscle (which is adjacent to the toxin injected left gastrocnemius muscle of the rat) to the weight of the uninjected right biceps femoris muscle of the same rat. The x axis shows the amount in units of the *botulinum* toxin type A that was injected into the left gastrocnemius muscle.

FIG. 13 shows the result of this experiment where the left gastrocnemius muscle of different rats was injected with varying amounts of a *botulinum* toxin type A. The y axis shows the ratio (as a percent) of the weight of the uninjected left soleus muscle (which is adjacent to the toxin injected left gastrocnemius muscle of the rat) to the weight of the uninjected right soleus muscle of the same rat. The x axis shows the amount in units of the *botulinum* toxin type A that was injected into the left gastrocnemius muscle.

As shown by FIGS. 11–13 injection of BOTOX® caused muscle atrophy (and muscle weight decrease) at the injection muscle (left gastrocnemius) and adjacent (left bicep femoris and left soleus muscles) sites. The injected left gastrocnemius muscle showed an excellent dose-related decrease in muscle weight that was well modeled with a statistical function (4-parameter logistic regression). An ED50 (the dose required to reach 50% of the maximum possible level of response) for the muscle weight response was calculated (0.47 U/rat) and is associated with a very good confidence interval (standard error=0.03), showing therefore that this is a feasible and precise in vivo method for assessing pharmacologic potency of a *botulinum* toxin, such as BOTOX®. Muscle weight reduction is a more sensitive endpoint than lethality since the ED50 dose for rat muscle weight (0.47 U) is more than 2-fold lower than the mouse LD50 assay on a unit per animal basis. Muscles being injected showed a lower ED50 than the adjacent muscles (0.65 U for left biceps femoris and 1.16 U for left soleus) into which the toxin diffused from the injected gastrocnemius muscle. The ratio of ED50 of an adjacent muscle to the gastrocnemius can be used as a measure of the diffusion of BOTOX®. These data support the use of muscle weight to assess potency and diffusion in a single test system.

An assessment of potency of a *botulinum* toxin with the assays disclosed herein to measure muscle atrophy and muscle weight subsequent to an intramuscular (IM) injection of a *botulinum* toxin is more clinically relevant than the current standard. The current standard (mouse IP LD50 potency assay) involves an intraperitoneal (IP) injection followed by monitoring for mortality in the mouse. However, since *botulinum* toxin is typically used IM (never IP), intramuscular exposure is more clinically relevant. Furthermore, the IM approach allows calculation of an effective dose per unit of muscle mass (dose per gram of muscle), which can permit clinicians to determine how much of a *botulinum* toxin to inject into muscles of various sizes.

Additionally, the muscle weight and atrophy assay disclosed herein is a useful tool for assessing diffusion of a *botulinum* toxin, which is an important property to evaluate in new formulation development for *botulinum* toxins. A slight diffusion within the injected muscle is necessary to achieve a full therapeutic response while extensive diffusion to distal sites are always undesirable as this may result in serious adverse side effects. In optimizing a formulation, one has to understand the degree of desirable diffusion for treating a specific clinical condition. A determination of the weight and atrophy of muscles adjacent and distal to the injection site can provide critical information on whether a new formulation is potentially useful.

While this invention has been described with respect to various specific examples and embodiments, it is to be understood that the invention is not limited thereto and that it can be variously practiced with the scope of the following claims. All patents, applications, publications and references cited herein are incorporated by reference in their entireties.

What is claimed is:

1. A method for determining an effect of a *botulinum* neurotoxin upon a muscle, the method comprising the steps of: (a) administering a *botulinum* neurotoxin to a muscle of a mammal, (b) staining muscle nuclei present in a muscle sample of the muscle, each of the muscle nuclei having a size; (c) determining a nuclei density and/or nuclei area of the muscle sample by measuring the size of each of one or more stained muscle nuclei located in the muscle sample; and (d) comparing the nuclei density and/or nuclei area of the muscle sample to a nuclei density and/or nuclei area of a muscle that was not administered a *botulinum* neurotoxin.

2. The method of claim 1 wherein *botulinum* neurotoxin is selected from the group consisting of *botulinum* neurotoxin types A, B, $C_1$, D, E, F, G, and mixtures thereof.

3. The method of claim 1 wherein the *botulinum* neurotoxin is a *botulinum* toxin type A.

4. The method of claim 1, wherein the muscle sample has a plurality of muscle nuclei, and step (c) further comprises a step of counting the number of muscle nuclei in an area of the muscle sample.

5. A method for determining a muscle atrophy, the method comprising the steps of: (a) administering a *botulinum* neurotoxin to a muscle; (b) staining muscle nuclei present in a muscle sample of the muscle, each of the muscle nuclei having a size; (c) measuring a first nuclei density and/or nuclei area of the muscle sample by measuring the size of each of one or more stained muscle nuclei, and; (d) comparing the first nuclei density and/or nuclei area with a second nuclei density and/or nuclei area of a muscle sample of muscle which has not been administered with a *botulinum* neurotoxin, thereby determining a muscle atrophy.

6. The method of claim wherein 5 wherein the *botulinum* neurotoxin comprises a *botulinum* neurotoxin selected from the group consisting of *botulinum* neurotoxin types A, B, $C_1$, D, E, F, G and mixtures thereof.

7. The method of claim 5, wherein the *botulinum* neurotoxin is a *botulinum* neurotoxin type A.

8. The method of claim 5, wherein the muscle sample has a plurality of muscle nuclei, and step (c) further comprises a step of counting the number of muscle nuclei in an area of the muscle sample.

9. A method of determining a potency of a *botulinum* neurotoxin, the method comprising the steps of:
(a) administering a *botulinum* neurotoxin to a muscle; (b) staining muscle nuclei present in a muscle sample of the muscle, each of the muscle nuclei having a size; (c) measuring a first nuclei density and/or nuclei area of the muscle sample by measuring the size of each of one or more stained muscle nuclei, and; (d) comparing the first nuclei density and/or nuclei area with a second nuclei density and/or nuclei area of a muscle sample of muscle which has not been administered a *botulinum* neurotoxin, thereby determining a potency of a *botulinum* toxin.

10. The method of claim 9, wherein the *botulinum* neurotoxin is a *botulinum* neurotoxin type A.

11. The method of claim 9, wherein the muscle sample has a plurality of muscle nuclei, and step (c) further comprises a step of counting the number of muscle nuclei in an area of the muscle sample.

* * * * *